United States Patent [19]

Robblee

[11] Patent Number: 4,997,526

[45] Date of Patent: Mar. 5, 1991

[54] ASSAYING FOR A BIOLOGICALLY ACTIVE COMPONENT

[75] Inventor: Lois S. Robblee, Randolph, Mass.

[73] Assignee: EIC Laboratories, Inc., Norwood, Mass.

[21] Appl. No.: 713,469

[22] Filed: Mar. 19, 1985

[51] Int. Cl.$^5$ .................................. G01N 27/327
[52] U.S. Cl. .............................. 204/153.2; 436/806; 436/518
[58] Field of Search ............... 204/1 T, 1 E, 403, 412; 436/806; 435/817

[56] References Cited

U.S. PATENT DOCUMENTS

| | | | |
|---|---|---|---|
| 4,198,389 | 4/1980 | Wadsworth | 436/806 X |
| 4,216,065 | 8/1980 | Rechnitz et al. | 204/1 E |
| 4,233,144 | 11/1980 | Pace et al. | 204/1 T X |
| 4,321,123 | 3/1982 | Nakamura et al. | 204/403 |
| 4,352,884 | 10/1982 | Nakashima et al. | 204/403 X |
| 4,402,819 | 9/1983 | Rechnitz et al. | 204/418 |
| 4,444,879 | 4/1984 | Paulus | 204/403 X |
| 4,490,216 | 12/1984 | McConnell | 204/1 T |

OTHER PUBLICATIONS

Lane et al., "Application of Semidifferential Electroanalysis to Studies of Neurotransmitters in the Central Nervous System", J. Electroanal. Chem., 95, 117–122 (1979).
Aizawa et al., "Enzyme Immunosensor", Anal. Biochem., 94, 22–29 (1979).
Lane et al., "Diff. Double Pulse Volt. at Chem. Modified Pt. Electrodes for in Vivo Determination of Catecholamines", Anal. Chem., 48, 1287 (1976).
Aizawa, M. et al., Anal. Chem. Acta, 115, 61–67 (1980).
Aizawa, M. et al., J. Solid-Phase Biochem., 4, 25–31 (1979).
Aizawa, M. et al., J. Memb. Sci., 4, 221–228 (1978).
Alexander, P. W. and Maltra, C., Anal. Chem., 54, 68–71 (1982).
Boitieux, J-L. et al., Clin. Chem., 25, 318–321 (1979).
Collins, S., and Janata, J., Anal. Chim. Acta., 136, 93–99 (1982).
Karube, I. et al., Anal. Chim. Acta, 156, 283–287 (1984).
Keating, M. Y. and Rechnitz, G. A., Anal. Chem., 56, 801–806 (1984).
Keating, M. Y. and Rechnitz, G. A., Analyst, Jun., 766–768 (1983).
Mattiasson, B. and Nilsson, H., FEBS Letters, 78, 251–254 (1977).
Meyerhoff, M. and Rechnitz, G. A., Science, 195, 494–495 (1977).
Solsky, R. L. and Rechnitz, G. A., Science, 204, 1308–1309 (1979).
Yamamoto, N. et al., Clin. Chem., 26, 1569–1572 (1980).
Yamamoto, N. et al., Chem. Letters, No. 3, 245–246 (1978).
Yamamoto, N. et al., J. Immunol. Methods., 22, 309–317 (1978).
Yamamoto, N. et al., "Potentiometric Detection of Biological Substances by using Chemically Modified Electrodes", (F108), pp. 699–714 (no citation).

Primary Examiner—Nam X. Nguyen
Attorney, Agent, or Firm—Fish & Richardson

[57] ABSTRACT

A liquid mixture is assayed for a biologically active component that undergoes a reduction or oxidation reaction within a specific voltage range by immobilizing at an electrically conductive surface, a binding partner for the component, exposing the surface to the component to permit complexing to occur, applying a voltage to the surface in a range which will cause the component to undergo an oxidation or reduction reaction, and measuring the resulting current as an indication of the presence of the component.

7 Claims, 3 Drawing Sheets

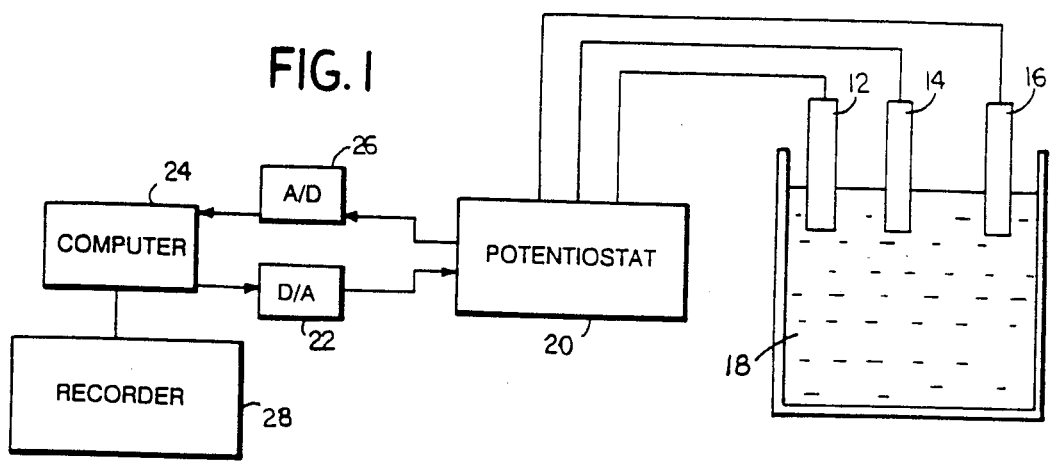
FIG. 1
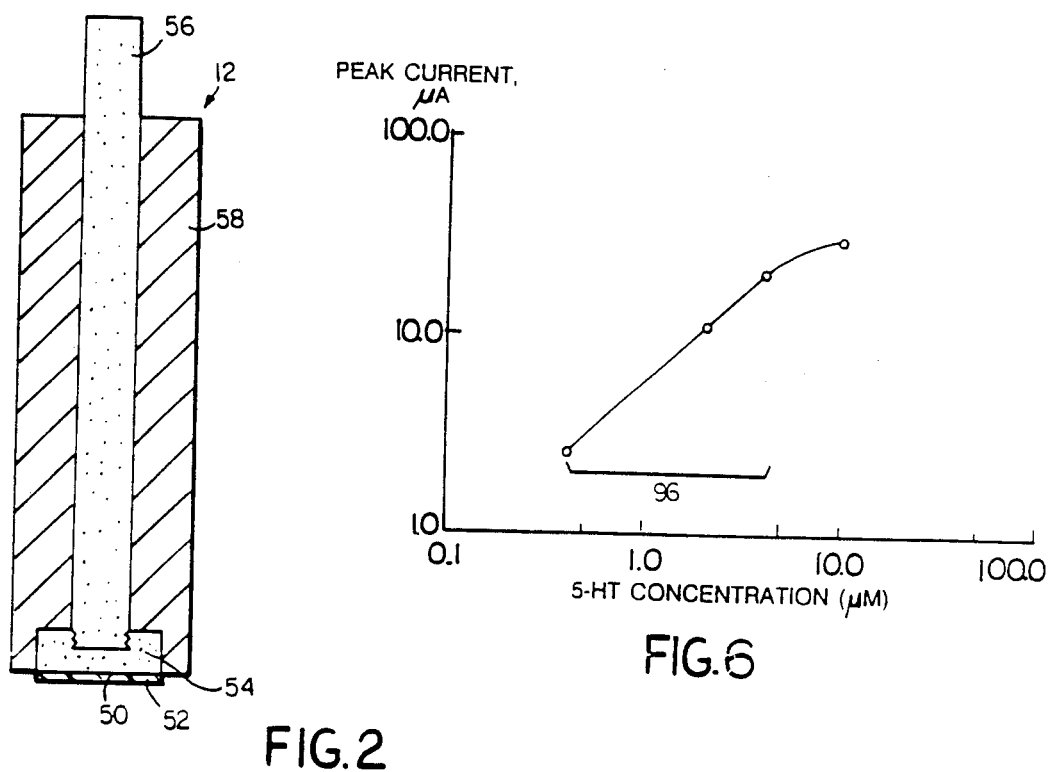
FIG. 2
FIG. 6

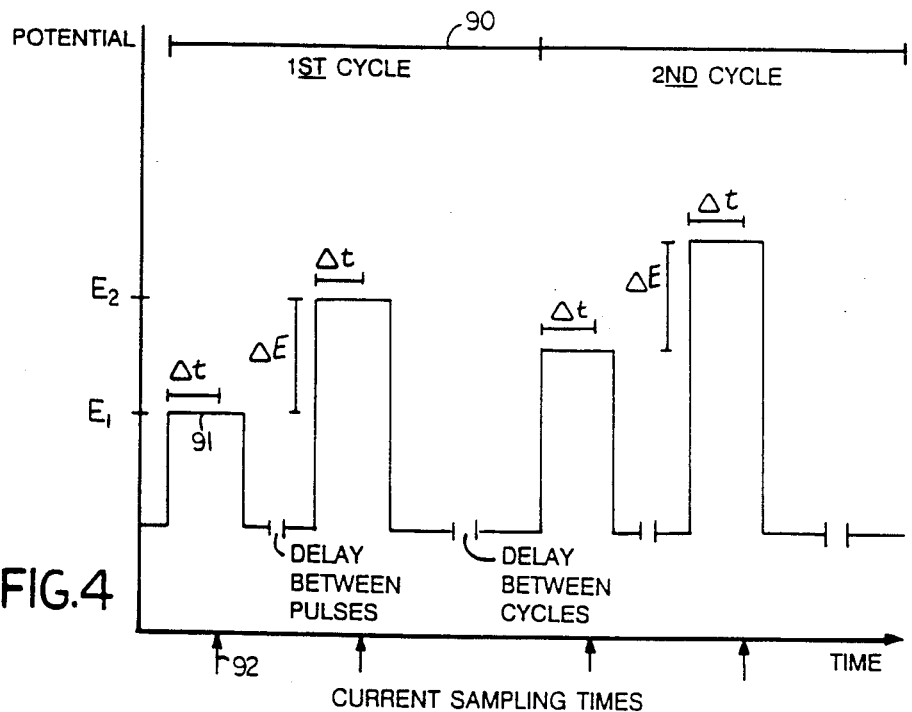
FIG.4
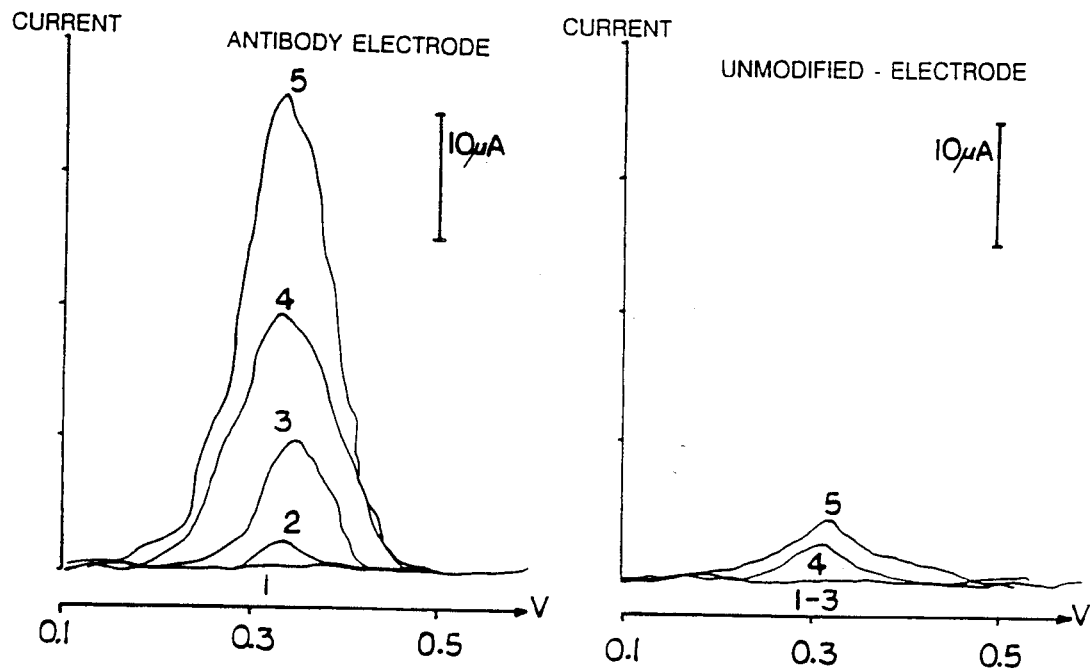
FIG.5A
FIG.5B 4,997,526

ASSAYING FOR A BIOLOGICALLY ACTIVE COMPONENT

BACKGROUND OF THE INVENTION

This invention relates to assaying a liquid mixture for a particular biologically active component.

The component may be present only in minute quantities in a complex mixture such as blood or urine, which may also contain molecules of similar structure to the component of interest.

In one method for determining the concentration of such a component (for example, the method disclosed in Lane et al., *J. Electroanal. Chem.* 95: 117–122 (1979)), a voltage sweep is applied between a reference electrode and a working electrode to oxidize or reduce the component. The resulting current, which flows between the working electrode and a counter electrode, is measured as an indication of the concentration of the component in the liquid mixture.

In another method, disclosed in Yamamoto et al., *J. Immuno. Methods* 22: 309–317 (1978), the presence of an antigen component is determined by immobilizing on the working electrode antibodies which are binding partners to the antigen component, and allowing the antigen component molecules to bind to the antibodies to form a charged layer. The presence of the charged layer is detected as an indication of the presence of the antigen component.

In a third method, disclosed in Aizawa et al. *Anal. Biochem.* 94: 22–28 (1979), the concentration of an antigen component is measured by a series of steps which include adding to the liquid mixture an additional amount of the antigen component labeled with an enzyme, allowing both the labeled and non labeled antigens to compete for antibody binding sites, providing a substance which is acted upon by the enzyme associated with the bound labeled antigens to cause the release of a reporter substance, and measuring the reporter substance as an indication of concentration.

SUMMARY OF THE INVENTION

The general feature of the invention is that a binding partner for the component to be assayed is immobilized at an electrically conductive surface, the surface is exposed to the component to permit the component to bind to the binding partner, a voltage is applied to the surface in a range which will cause the component to undergo an oxidation or reduction reaction, and the resulting current is measured as an indication of the presence of the component.

Preferred embodiments include the following features. The binding partner offers enough binding sites to prevent the sites from being saturated prior to the voltage being applied. The component is a hapten such as 5 HT and the binding partner is an antibody such as anti 5 HT. The voltage is varied using a double differential pulse technique. The voltage can be applied either while the surface remains exposed to the original mixture or the surface is exposed to another electrolyte.

The resulting current curve against voltage produces a selective and sensitive indication of the concentration of the component in the mixture, and the electrode can be reused.

Other advantages and features of the invention will become apparent from the following description of the preferred embodiment and from the claims.

DESCRIPTION OF THE PREFERRED EMBODIMENT

We first briefly describe the drawings.

Drawings

FIG. 1 is a diagram of an assaying system.

FIG. 2 is a cross sectional view of a working electrode for use in the system of FIG. 1.

FIG. 4 is a diagram of a voltage profile.

FIG. 5A, 5B are graphs of current against voltage.

FIG. 6 is a graph of peak current against concentration.

STRUCTURE

Figure 3A:
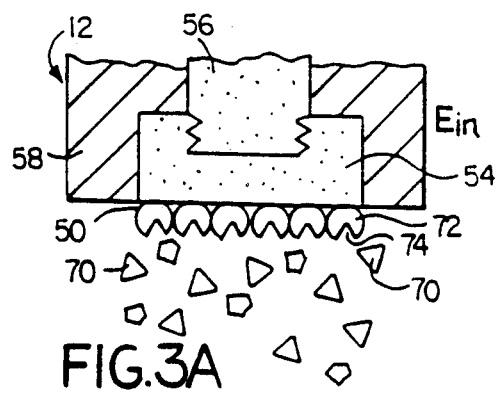
FIG. 3 is a series of schematic diagrams of the activity at the working electrode.

Referring to FIG. 1, working, reference, and counter electrodes 12, 14, 16 have their ends immersed in a liquid sample 18 containing an unknown concentration of serotonin (5-hydroxytryptamine, or 5-HT). Sample 18 may also contain substances which have a similar molecular structure to serotonin or which have a similar oxidation potential as serotonin. The three electrodes are electrically connected by separate wires to a potentiostat 20 capable of applying a variable voltage between the working and reference electrodes 12, 14, and of sensing current flowing between the working and counter electrodes 12, 16. Potentiostat 20 is connected via a digital-to-analog converter 22 to a digital computer 24, which supplies signals to control the voltage which is delivered by the potentiostat. Computer 24 is also connected via an analog-to-digital converter 26 to potentiostat 20 to receive signals that represent the current flowing. A recorder 28 is connected to computer 24 to record the voltage and current information. Reference electrode 14 is a saturated calomel electrode (SCE). Counter electrode 16 is metallic, for example, Pt.

Referring to FIG. 2, electrode 12 has a surface 50 on which anti-5-HT antibody molecules 52 have been immobilized by chemisorption (immersing the cleaned surface 50 in a solution containing the antibody molecules for 1 to 18 hours at 4° C.) or by covalent attachment. Surface 50 is the bottom face of a glassy carbon disk 54 which is screw mounted on one end of a copper rod 56. An insulating, polytetrafluoroethylene coating 58 covers rod 56 except for an exposed section at its free end where a wire (not shown in FIG. 2) is connected. Coating 58 also covers disk 54 except for its surface 50.

Operation

Figure 3B:
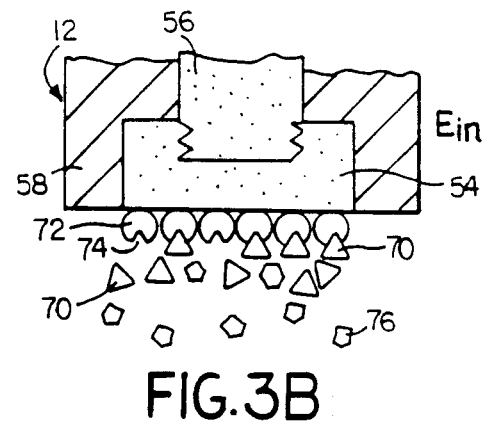

To determine the concentration of 5-HT, the disk end of electrode 12 is immersed in sample 18 and an initial potential ($E_{in}$) is applied between the working and reference electrodes. $E_{in}$ is small enough (e.g., −0.4 volts vs. SCE) as to cause no electrochemical activity. Referring to FIGS. 3A, 3B, 5-HT molecules 70 in sample 18 bind to (i.e., complex with) anti 5-HT molecules 72 at binding sites 74. Diffusion of 5-HT molecules within sample 18 provides a continuing supply of 5-HT molecules for bindingg. Thus, 5-HT molecules are concentrated at surface 50 over time. Other types of molecules 76 in sample 18 which are not binding partners of the anti-5-HT molecules do not bind at binding sites 74.

At a time before all of the binding sites 74 are saturated by 5-HT molecules 70, a differential double pulse voltammetric (DDPV) measuring procedure, of the kind described in Lane et al., *Anal. Chem.* 48: 1287 (1976), is begun.

Referring to FIG. 4, the DDPV procedure is conducted in a series of cycles 90. In each cycle two successive voltage pulses 91 which differ in amplitude by a predetermined amount $\Delta E$ are applied between the working and reference electrodes. Towards the end of each pulse ($\Delta t$ after the beginning of the pulse), current between the working and counter electrodes is sampled at a time 92. The difference between the two currents corresponding to the two pulses of each cycle, called $\Delta i$, is stored. In each successive cycle the pulses are slightly higher in amplitude, but the values $\Delta E$ and $\Delta t$ remain the same. The amplitudes are selected to span a range which includes the oxidation potential, $E_{ox}$, of 5-HT. The values of $\Delta i$ are then plotted against voltage. A peak occurs at the oxidation potential of 5-HT, i.e., approximately 0.35 volts vs. SCE. The magnitude of the peak is in proportion to the concentration of 5-HT reacting at the electrode surface.

Figure 3C:
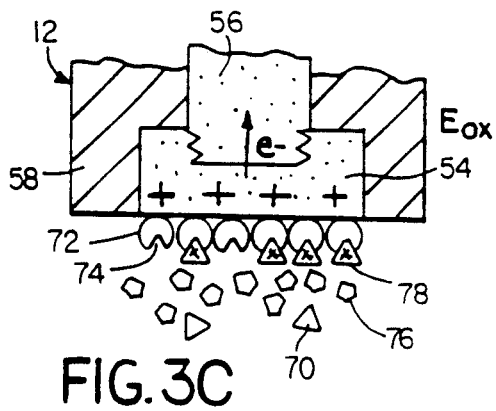

Referring to FIG. 3C, when the potential $E_{ox}$ is applied to electrode 12, bound 5-HT molecules 70 are oxidized, giving up electrons which then flow to electrode disk surface 50 creating a current. The oxidized 5-HT molecules 78 are released from the binding sites. Because of diffusion within the solution, a number of 5-HT and other types of free molecules in the liquid mixture will, during the current measurements, be near enough (e.g. 20 Angstroms) to electrode 12 to also be oxidized and thus to contribute to the measured current. However, because of the relatively high concentration of bound 5-HT, the contribution of the free molecules to the current signal will be small.

For example, referring to FIG. 5A, solutions of phosphate-buffered saline (PBS) containing different selected concentrations of 5-HT produced different corresponding peak amplitudes at the oxidation potential. Figs. 5A, 5B were obtained using a glassy carbon electrode. The curve labeled 1, 2, 3, 4, and 5, represent, respectively, 0, 0.4, 2, 4, and 10 micromolar concentrations of 5-HT.

Referring to FIG. 6, the relationship between the peak currents and concentrations of FIG. 5A is linear over a range 96 of concentrations.

Referring to FIG. 5B, for an otherwise identical electrode lacking anti 5-HT molecules, the peak currents are substantially smaller.

During the course of the measurement, all of the 5-HT molecules are oxidized and released into the liquid mixture, leaving the electrode free of 5-HT molecules. The electrode can then be reused for a subsequent measurement performed in the same way.

Figure 3D:
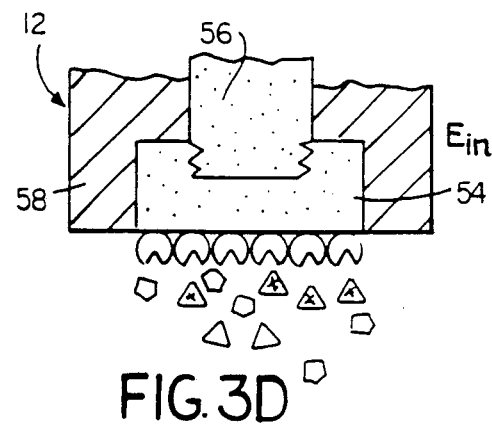

Referring to FIG. 3D, after a set of current measurement cycles are finished, the initializing potential, $E_{in}$, is again applied to electrode 12 and a new measurement can be performed.

The peak current reading depends on the length of time during which the 5-HT molecules are permitted to bind to the anti-5-HT molecules, the concentration of 5-HT molecules in solution, and the concentration of bound 5-HT molecules By adjusting the time the electrode is in contact with the sample solution containing 5-HT, or by adjusting the time between successive potential sweeps, or, for a fixed time, adjusting the extent of surface coverage by immobilized anti-5-HT molecules, the measured current can be made to correspond linearly to the concentration of 5-HT in the sample solution.

Immobilizing the anti-5-HT molecules on the electrode makes the electrode specifically susceptible to 5-HT binding. Concentrating the 5-HT antibody molecules on the electrode surface improves the sensitivity of the measured current to the concentration of 5-HT in solution, and reduces the influence of the diffusion of other molecules of similar structure close to the electrode on the current measurements.

In measurements of the type shown in FIG. 5, the technique has been shown to have a 20 fold greater sensitivity for 5-HT over 5-hydroxy-indoleacetic acid (5-HIAA), a metabolite of 5-HT which has a similar oxidation potential. The electrode's response to a 2 $\mu M$ 5-HT was found to be unaffected by adding 5-HIAA concentrations as great as 30 $\mu M$.

Other Embodiments

Other embodiments are within the following claims. For example, other voltammetric techniques such as linear voltage sweeping can be used. The electrode can be removed from the liquid mixture and placed in a blank electrolyte, i.e., one which does not contain any 5-HT or molecules of similar structure or electroactivity. In this case, diffusion produces no additional contribution to current during the potential sweep. Any component in a liquid mixture can be assayed by immobilizing the appropriate binding partner on the electrode, provided that the molecule to be assayed can be oxidized or reduced over a reasonable potential range. The assay can be used to determine the presence, as well as the concentration of the molecules of interest. Other configurations of electrodes can be used, including the previously mentioned glassy carbon electrodes. The electrodes could be implanted for continuous or one time in vivo measurements.

I claim:

1. A method of assaying a liquid mixture for a biologically active component that is characterized by undergoing a reduction or oxidation reaction in response to the application of a voltage level that is within the range of voltage levels over which said reaction occurs, said method comprising:

providing an electrically conductive surface, immobilizing at said surface a binding partner capable of selectively complexing with said component, exposing said surface to said mixture;

applying a voltage within said range between said surface and said mixture to cause said component that has complexed with said immobilized binding partner to undergo said reaction;

varying said voltage with time according to a predetermined profile; and measuring a current that results from said reaction caused by applying said voltage, as an indication of the presence of said component in said liquid mixture.

2. The method of claim 1 wherein said profile is a linear voltage sweep with time.

3. The method of claim 1 or 2 wherein a plurality of complexing sites are immobilized at said conductive surface, and said exposing step comprises exposing said conductive surface to said mixture for a time that allows said component to complex at some but not all of said sites.

4. The method of claim 1 or 2 wherein after said exposing step said surface is exposed to a blank electrolyte for said measurement.

5. A method of assaying a liquid mixture for a biologically active component that is characterized by undergoing a reduction or oxidation reaction in response to the application of any voltage level that is within a range of voltage levels over which said reaction occurs, said method comprising:

provide an electrically conductive surface, immobilizing at said surface a binding partner capable of selectively complexing with said component, exposing said surface to said mixture;

applying a voltage within said range between said surface and said mixture to cause said component that has complexed with said immobilized binding partner to undergo said reaction, varying said voltage in according with a double differential pulse technique, and measuring a current that results from said reaction caused by applying said voltage, as an indication of the presence of said component in said liquid mixture.

6. The method of claim 5 wherein a plurality of complexing sites are immobilized at said conductive surface, and said exposing step comprises exposing said conductive surface to said mixture for a time that allows said component to complex at some but not all of said sites.

7. The method of claim 5 or 6 wherein after said exposing step said surface is exposed to a blank electrolyte for said measurement.

* * * * *